(12) United States Patent
Tung et al.

(10) Patent No.: US 9,381,069 B2
(45) Date of Patent: Jul. 5, 2016

(54) MEDICAL INSTRUMENT HOLDING APPARATUS

(71) Applicant: Hiwin Technologies Corp., Taichung (TW)

(72) Inventors: Cheng Wei Tung, Taichung (TW); Ren Jeng Wang, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 326 days.

(21) Appl. No.: 14/184,839

(22) Filed: Feb. 20, 2014

(65) Prior Publication Data
US 2015/0230866 A1   Aug. 20, 2015

(51) Int. Cl.
*A61B 17/14* (2006.01)

(52) U.S. Cl.
CPC ..................................... *A61B 90/57* (2016.02)

(58) Field of Classification Search
CPC ............... A61B 19/0256; A61B 19/26; A61B 2019/267; A61B 19/02; F16M 13/02
USPC ........................ 600/102, 112, 114; 606/1, 130
See application file for complete search history.

(56) References Cited

U.S. PATENT DOCUMENTS

| | | | | |
|---|---|---|---|---|
| 5,697,939 A * | 12/1997 | Kubota | ................. | A61B 19/201 606/130 |
| 2002/0026190 A1* | 2/2002 | Walulik | ................. | A61B 17/66 606/57 |
| 2003/0199738 A1* | 10/2003 | Yager | ..................... | A61B 17/02 600/227 |
| 2004/0186346 A1* | 9/2004 | Smith | .................... | A61M 29/00 600/102 |
| 2005/0080321 A1* | 4/2005 | Bjork | ....................... | A61B 1/32 600/230 |
| 2005/0234293 A1* | 10/2005 | Yamamoto | ......... | A61B 1/00082 600/102 |
| 2005/0272981 A1* | 12/2005 | Bjork | ..................... | A61B 19/26 600/227 |
| 2006/0211920 A1* | 9/2006 | Bethke | ............... | A61B 17/0206 600/234 |
| 2006/0231713 A1* | 10/2006 | Crain | ..................... | F16M 13/02 248/309.1 |
| 2007/0120025 A1* | 5/2007 | Wilson | .................... | B25B 5/101 248/125.7 |
| 2007/0200036 A1* | 8/2007 | Hsieh | ..................... | F16M 11/28 248/122.1 |
| 2007/0267556 A1* | 11/2007 | Herskovic | ............ | A61G 7/0503 248/218.4 |
| 2009/0182196 A1* | 7/2009 | Kefer | ..................... | A61B 1/0052 600/114 |
| 2009/0192520 A1* | 7/2009 | Finlay | .................... | A61B 19/00 606/130 |
| 2011/0101587 A1* | 5/2011 | Quintania | ............... | B25B 5/006 269/74 |
| 2012/0035415 A1* | 2/2012 | Doyle | .................. | A61B 1/0014 600/102 |
| 2012/0118098 A1* | 5/2012 | Doyle | .................... | G05G 11/00 74/490.12 |
| 2014/0034799 A1* | 2/2014 | Fallows | ............... | F16M 11/046 248/297.21 |
| 2014/0054522 A1* | 2/2014 | Panzer | ...................... | B66F 3/10 254/98 |
| 2015/0133958 A1* | 5/2015 | Singh | ..................... | A61B 19/20 606/130 |
| 2015/0223898 A1* | 8/2015 | Merlo | .................... | A61B 19/26 211/85.13 |
| 2016/0009349 A1* | 1/2016 | Kooi, Jr. | ............... | B63H 20/106 440/6 |

* cited by examiner

*Primary Examiner* — Amy R Weisberg
(74) *Attorney, Agent, or Firm* — Charles E. Baxley

(57) ABSTRACT

A medical instrument holding apparatus includes an attachment device attached to a longitudinal shaft and having a casing, a coupling device attached to the casing of the attachment device, and a carrying device attached to the coupling device, and the carrying device includes an orifice and an aperture, and the aperture of the carrying device is tilted and inclined relative to the orifice of the carrying device, a medical instrument includes an insertion tube engaged into the orifice of the carrying device, and a projecting device is engaged in the aperture of the carrying device for projecting a light onto the insertion tube of the medical instrument at an index mark.

7 Claims, 3 Drawing Sheets

MEDICAL INSTRUMENT HOLDING APPARATUS

BACKGROUND OF THE INVENTION

1. Field of the Invention

The present invention relates to a medical instrument holding apparatus, and more particularly to a medical instrument holding apparatus including an improved or simplified structure or configuration that may be easily and quickly made or manufactured by the manufacturers and that may be easily used to conduct the operation on the patient, and that may be used or provided for easily and quickly and effectively indicating or locating the remote of center motion (RCM) or index mark in the animal or human body or the other objects and for allowing the medical surgery or medical operation to be easily conducted or actuated by the users or operators.

2. Description of the Prior Art

Typical medical instruments, such as rigidoscopes, laparoscopes, endoscopes, trocars, treating instruments, or the other medical instruments or the like have been developed and widely provided and used for conducting or operating an operation on a patient, and are typically grasped and held by the hands of the operators, such as the doctors, and it will be difficult for the operators or the doctors to hold the medical instruments and to conduct or operate the operation on the patient.

Normally, the medical instruments are grasped and held by one of the operators or the doctors, and the other operator or doctor will stand beside the medical instruments holding operator and will both standing near the patient at the same time, in a tiny or narrowed operation room.

For allowing the medical instruments to be held in place without being grasped by the operators or the doctors, a scope-holder has been disclosed and used to hold the medical instruments in place, for inserting the medical instruments into the abdominal cavity of a patient.

For example, U.S. Pat. No. 5,697,939 to Kubota et al. discloses one of the typical medical instrument holding apparatuses comprising a plurality of arms sections and holding sections for holding and grasping the treating instrument or medical instrument and for engaging or inserting the treating or medical instruments into the abdominal cavity of the patient.

However, the typical medical instrument holding apparatuses comprise a rather complicated structure or configuration having a number of parts or elements that may not be easily and quickly made or manufactured and that may not be easily used to conduct the operation on the patient.

The present invention has arisen to mitigate and/or obviate the afore-described disadvantages of the conventional medical instrument holding apparatuses.

SUMMARY OF THE INVENTION

The primary objective of the present invention is to provide a medical instrument holding apparatus including an improved or simplified structure or configuration that may be easily and quickly made or manufactured by the manufacturers and that may be easily used to conduct the operation on the patient.

The other objective of the present invention is to provide a medical instrument holding apparatus including an improved or simplified structure or configuration that may be used or provided for easily and quickly and effectively indicating or locating the remote of center motion (RCM) or index mark in the animal or human body or the other objects and for allowing the medical surgery or medical operation to be easily conducted or actuated by the users or operators.

In accordance with one aspect of the invention, there is provided a medical instrument holding apparatus comprising a longitudinal shaft, an attachment device attached to the longitudinal shaft, the attachment device including a casing, a coupling device attached to the casing of the attachment device, a carrying device attached to the coupling device, and the carrying device including an orifice and an aperture formed therein, the aperture of the carrying device being tilted and inclined relative to the orifice of the carrying device, a medical instrument including an insertion tube extended therefrom and engaged into the orifice of the carrying device, and a projecting device engaged in the aperture of the carrying device for projecting a light onto the insertion tube of the medical instrument and for intersecting or contacting or engaging with the insertion tube of the medical instrument at a remote of center motion (RCM) or index mark, and the medical instrument holding apparatus includes an improved or simplified structure or configuration that may be easily and quickly made or manufactured by the manufacturers and that may be easily used to conduct the operation on the patient.

The aperture of the carrying device is tilted and inclined relative to the orifice of the carrying device for an included angle (a), for allowing the light projected by the projecting device to be intersected or contacted or engaged with the insertion tube of the medical instrument at a remote of center motion (RCM) or index mark.

The carrying device includes a middle portion having a groove for defining a spring blade in the middle portion of the carrying device, and arranged for allowing the orifice of the carrying device to be formed between the spring blade and the middle portion of the carrying device and for allowing the insertion tube of the medical instrument to be retained between the spring blade and the middle portion of the carrying device.

The carrying device includes a fastener engaged onto the middle portion of the carrying device and engaged through the groove of the carrying device and engaged with the spring blade for forcing the spring blade to move toward the middle portion of the carrying device and to secure the insertion tube of the medical instrument to the carrying device.

The carrying device includes a bracket having an engaging slot, such as a dove-tail slot formed therein, and the coupling device includes one or more, such as two spring biased catches engaged with the engaging slot of the bracket for detachably securing the carrying device to the coupling device.

The carrying device includes a narrowed neck segment extended therefrom, the spring biased catches are extended from the neck segment and include an outer diameter or outer dimension smaller than that of the neck segment of the coupling device for forming a peripheral shoulder between the spring biased catch and the neck segment and for engaging with the bracket of the carrying device.

The attachment device includes an engaging slot, such as a dove-tail slot formed in the casing, and the coupling device includes one or more, such as two spring biased arms extended outwardly therefrom and engaged with the engaging slot of the attachment device for detachably securing the coupling device to the attachment device.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
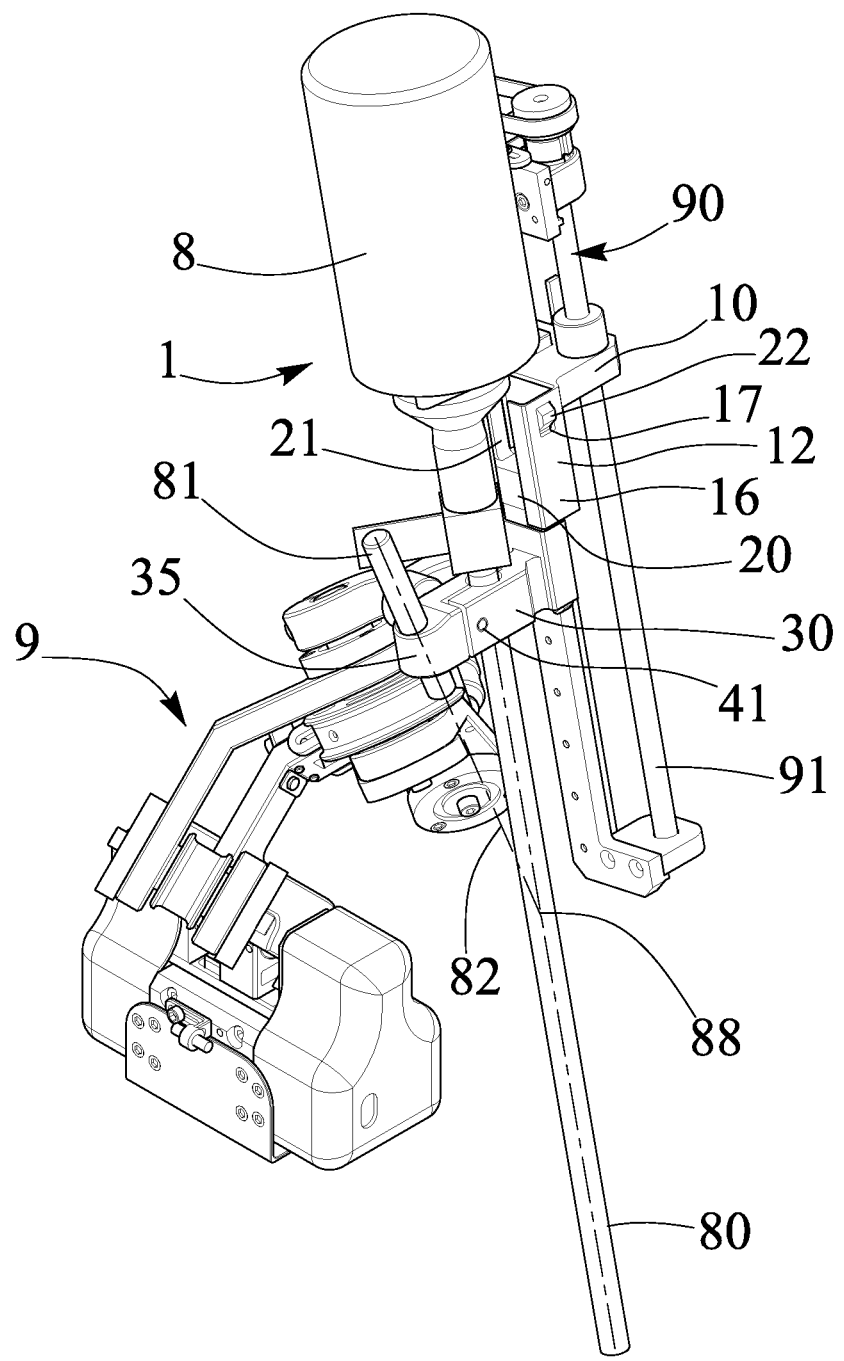
FIG. 1 is a perspective view illustrating the operation of a medical instrument holding apparatus in accordance with the present invention.
Figure 2:
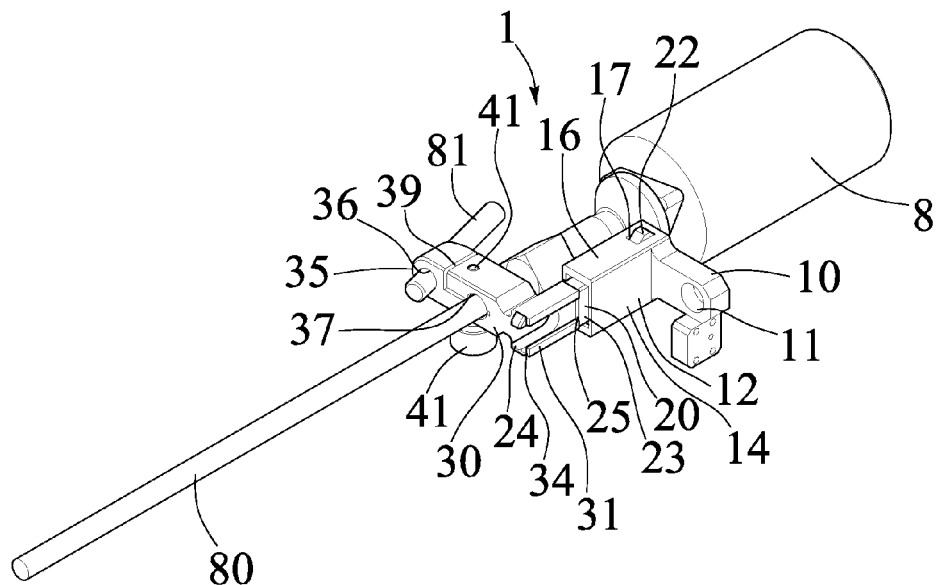
FIG. 2 is a perspective view of the medical instrument holding apparatus.
Figure 3:
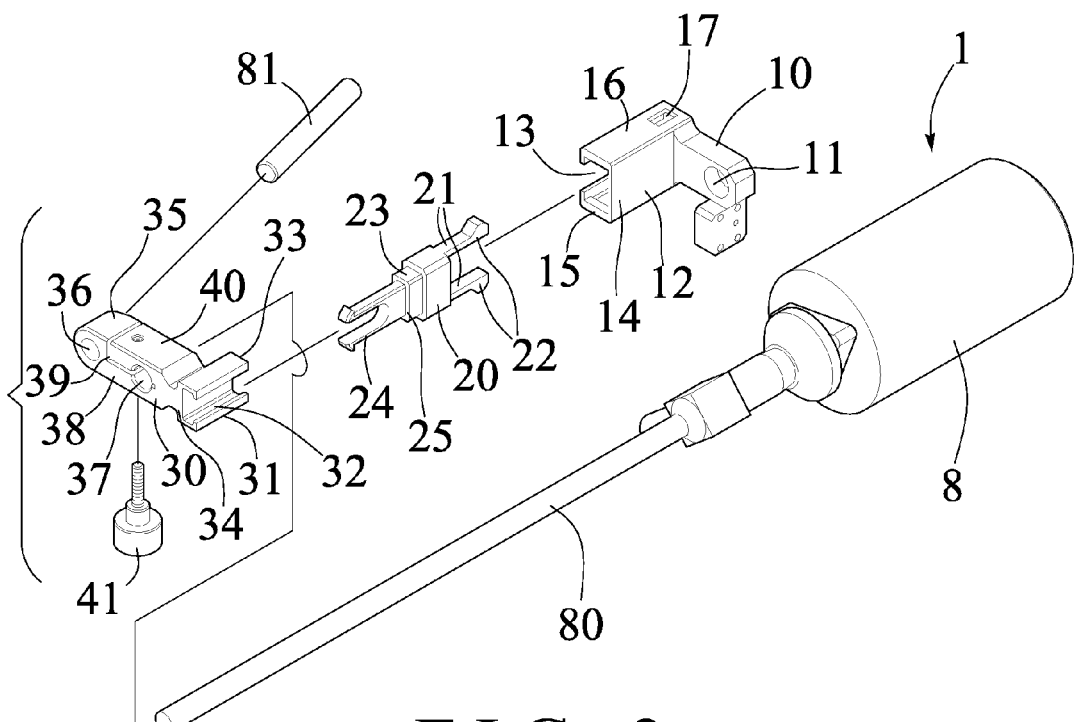
FIG. 3 is a partial exploded view of the medical instrument holding apparatus.

Referring to the drawings, and initially to FIGS. 1, 2 and 3, a medical instrument holding apparatus 1 in accordance with the present invention comprises a supporting device or mechanism 9 including a ball screw device or linear motion guide apparatus 90 or the like having a longitudinal rod or shaft 91 provided for slidably supporting or sustaining or engaging with a medical instrument 8, such as rigidoscope, laparoscope, endoscope, trocar, treating instrument, or the other medical instruments or the like, in which the medical instrument 8 normally includes an insertion tube 80 extended therefrom for inserting or engaging into the abdominal cavity of a patient (not illustrated), in which the ball screw device or linear motion guide apparatus 90 of the supporting mechanism 9 is typical and is not related to the present invention and will not be described in further details.

As also shown in FIGS. 1-3, the medical instrument holding apparatus 1 includes a connecting or coupling or attachment device 10 having a hole 11 formed therein for slidably receiving or engaging with the longitudinal shaft 91 of the linear motion guide apparatus 90 or of the supporting mechanism 9 and for being guided to slide or move along the longitudinal shaft 91. The sliding movement of the attachment device 10 along the longitudinal shaft 91 is also not related to the present invention and will not be described in further details. The attachment device 10 includes a bracket or frame or casing 12 having an engaging slot 13, such as a dove-tail slot 13 formed therein and formed or defined by a bottom or base wall 14 and two side walls 15, 16, and having a latch opening 17 formed in each of the side walls 15, 16 and communicating with the engaging slot 13 of the attachment device 10.

The medical instrument holding apparatus 1 further includes a catching or latching or coupling device 20 for being slidably received or engaged in the engaging slot 13 of the casing 12 of the attachment device 10, and the coupling device 20 includes one or more (such as two) legs or projections or spring biased arms 21 extended outwardly therefrom and parallel to each other, and the arms 21 each include a detent or peg or tongue 22 extended therefrom for selectively engaging with the latch opening 17 of the side wall 15, 16 of the casing 12 and for detachably or removably attaching or mounting or securing or coupling the coupling device 20 to the attachment device 10, the coupling device 20 includes a thickness reduced or narrowed portion or neck or segment 23 extended therefrom or formed or provided thereon and located distal to or opposite to the arms 21.

The coupling device 20 further includes a pair of spring biased projections or detents or tongues or catches 24 extended outwardly from the narrowed segment 23 and also located distal to or opposite to the arms 21, and the spring biased catches 24 includes an outer peripheral portion or contour or shape or size or diameter or dimension smaller than that of the narrowed segment 23 and/or of the coupling device 20 for forming or defining a peripheral shoulder 25 between the spring biased catches 24 and the narrowed neck segment 23. The medical instrument holding apparatus 1 further includes a catching or latching or coupling or supporting or sustaining or engaging or mounting or carrying device 30 to be detachably or removably attached or mounted or secured or coupled to the coupling device 20.

For example, the carrying device 30 includes another casing or block or frame or bracket 31 having an engaging slot 32, such as a dove-tail slot 32 formed therein for slidably receiving or engaging with the spring biased catches 24 of the coupling device 20 and for detachably or removably attaching or mounting or securing or coupling the carrying device 30 to the coupling device 20, in which one end or one or first or inner side 33 of the bracket 31 will be contacted or engaged with the peripheral shoulder 25 that is formed or provided on the neck segment 23 of the coupling device 20, and the spring biased catches 24 of the coupling device 20 will be contacted or engaged with the outer or the other or second side 34 of the bracket 31, and thus for detachably or removably attaching or mounting or securing or coupling the carrying device 30 to the coupling device 20.

The carrying device 30 further includes an outer or free end portion 35 having an orifice or aperture 36 formed therein for slidably receiving or engaging with a projector or projecting device 81, such as an index mark projecting device 81, and further includes an aperture or orifice 37 formed in the middle or intermediate portion 38 of the carrying device 30 for slidably or adjustably receiving or engaging with the insertion tube 80 of the medical instrument 8. The carrying device 30 further includes a manifold or cut slit or groove 39 formed in the middle or intermediate portion 38 thereof for forming or defining a spring blade 40 in the middle or intermediate portion 38 of the carrying device 30 and arranged for allowing the orifice 37 to be formed or defined between the spring blade 40 and the middle or intermediate portion 38 of the carrying device 30.

Figure 4:
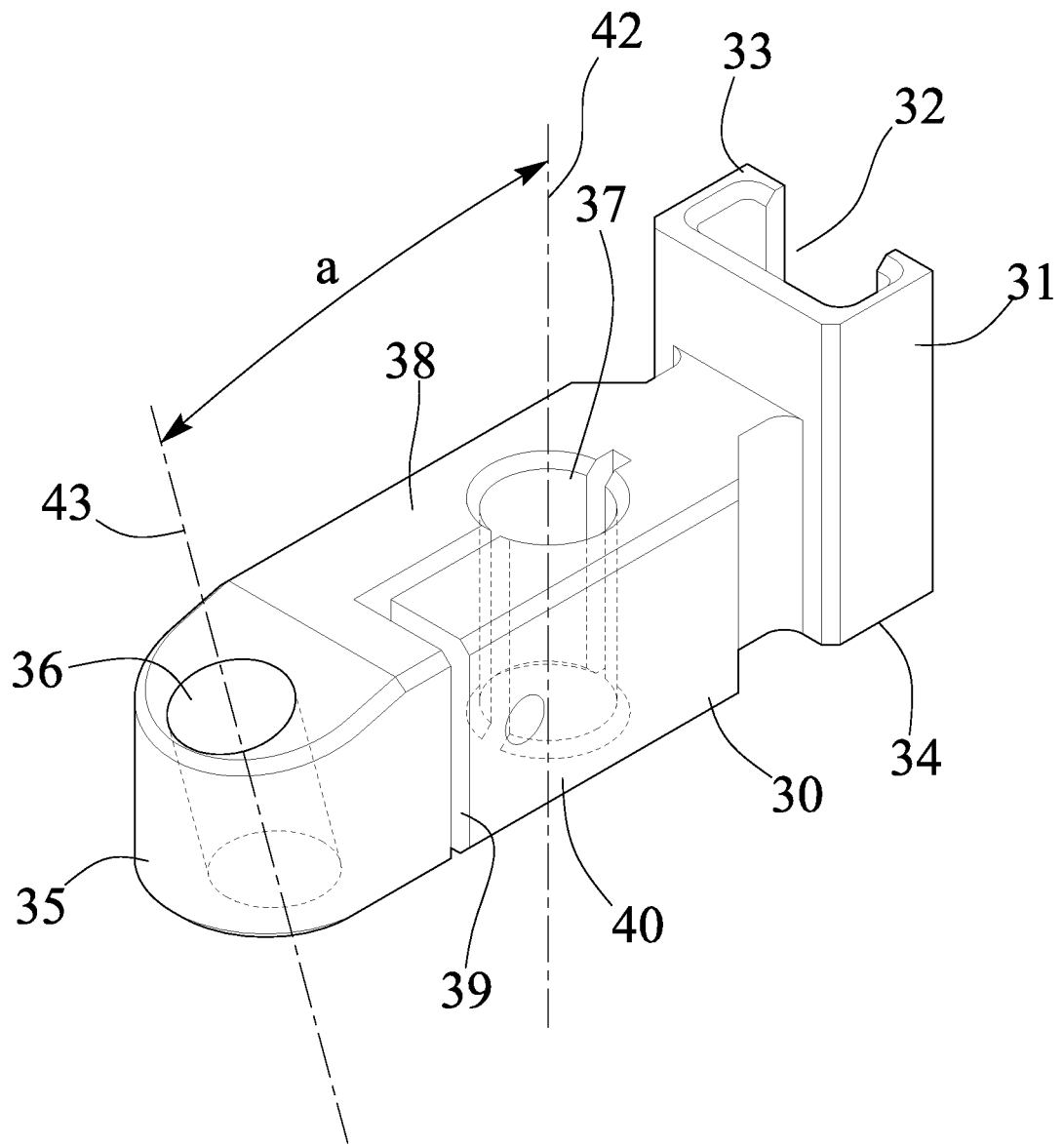
FIG. 4 is an enlarged partial perspective view illustrating the operation of the medical instrument holding apparatus.

A catch or latch or lock device or fastener 41 may further be provided and attached or mounted or secured or engaged onto the middle or intermediate portion 38 of the carrying device 30 and engaged through the groove 39 of the carrying device 30 and engaged with the spring blade 40 for selectively forcing the spring blade 40 to move toward the middle or intermediate portion 38 of the carrying device 30 and to solidly and stably anchor or retain or position or secure the insertion tube 80 of the medical instrument 8 to the carrying device 30. As shown in FIG. 4, the longitudinal axis 43 of the aperture 36 of the carrying device 30 is tilted or inclined relative to the longitudinal axis 42 of the orifice 37 of the carrying device 30 for an included angle (a), and arranged for allowing the light 82 (FIG. 1) emitted or projected by the projecting device 81 to be intersected or contacted or engaged with the insertion tube 80 of the medical instrument 8 at a remote of center motion (RCM) or index mark 88.

In operation, as shown in FIG. 1, the attachment device 10 of the medical instrument holding apparatus 1 in accordance with the present invention may be actuated or operated by the linear motion guide apparatus 90 or the like to move along the longitudinal shaft 91, and the medical instrument 8 may be attached or mounted or secured or coupled to the attachment device 10 with the coupling device 20 and the carrying device 30, and may be inserted or engaged into the abdominal cavity of the patient by the linear motion guide apparatus 90 of the supporting mechanism 9, and the projecting device 81 may emit or project the light 82 toward the insertion tube 80 of the medical instrument 8 at a remote of center motion (RCM) or index mark 88.

Accordingly, the medical instrument holding apparatus in accordance with the present invention includes an improved or simplified structure or configuration that may be easily and quickly made or manufactured by the manufacturers and that may be easily used to conduct the operation on the patient, and that may be used or provided for easily and quickly and effectively indicating or locating the remote of center motion (RCM) or index mark in the animal or human body or the other objects and for allowing the medical surgery or medical operation to be easily conducted or actuated by the users or operators.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

We claim:

1. An instrument holding apparatus comprising a coupling device, a carrier device and an attachment device,
    the carrier device having an orifice and an aperture formed thereon, the aperture being tilted and inclined relative to the orifice,
    a spring-biased catch arranged between the coupling device and the carrier device for detachably attaching the carrier device to the coupling device,
    said coupling device being attached to the attachment device and the attachment device being attached to a longitudinal shaft,
    said attachment device including an engaging slot and said coupling device including a spring biased arm extended outwardly therefrom and engaged with said engaging slot of said attachment device for detachably securing said coupling device to said attachment device,
    reception means engaging an instrument in working relationship with said carrying device, typically a medical instrument including an insertion tube extendable therefrom and engageable into said orifice of said carrying device, and
    a light-like tool engaged in said aperture of said carrying device for projecting a light onto said insertion tube of said medical instrument.

2. Said apparatus as claimed in claim 1, wherein said aperture of said carrying device is tilted and inclined relative to said orifice of said carrying device for an included angle (a), for allowing the light projected by said projecting device to be contacted with said insertion tube of said medical instrument at an index mark.

3. Said apparatus as claimed in claim 1, wherein said carrying device includes a middle portion having a groove for defining a spring blade in said middle portion of said carrying device, and arrange for allowing said orifice of said carrying device to be formed between said spring blade and said middle portion of said carrying device.

4. Said apparatus as claimed in claim 3, wherein said carrying device includes a fastener engaged onto said middle portion for said carrying device and engaged through said groove of said carrying device and engaged with said spring blade for forcing said blade to move toward said middle portion of said carrying device and to secure said insertion tube of said medical instrument to said carrying device.

5. Said apparatus as claimed in claim 1, wherein said carrying device includes a bracket having an engaging slot formed therein, and said coupling device includes a spring biased catch engaged with said engaging slot of said bracket for detachably securing said carrying device to said coupling device.

6. Said apparatus as claimed in claim 5, wherein said carrying device includes a narrowed neck segment extended therefrom, said spring biased catch is extended from said neck segment and includes an outer dimension smaller than that of said neck
    segment of said coupling device for forming a peripheral shoulder between said spring biased catch and said neck segment and for engaging with said bracket of said carrying device.

7. Said apparatus as claimed in claim 1, wherein said attachment device includes an engaging slot formed in said casing, and said coupling device includes a spring biased arm extended outwardly therefrom and engaged with said engaging slot of said attachment device for detachably securing said coupling device to said attachment device.

* * * * *